(12) United States Patent
Li et al.

(10) Patent No.: US 7,455,643 B1
(45) Date of Patent: Nov. 25, 2008

(54) CONTINUOUS NON-INVASIVE BLOOD PRESSURE MEASUREMENT APPARATUS AND METHODS PROVIDING AUTOMATIC RECALIBRATION

(75) Inventors: Luya Li, Coquitlam (CA); Rakesh Kumar Sethi, Vancouver (CA); Ming Sun, New Westminster (CA); Alexander Yuk Sit, Richmond (CA); Yong Liu, Vancouver (CA)

(73) Assignee: Nellcor Puritan Bennett Ireland, Galway (IE)

( * ) Notice: Subject to any disclaimer, the term of this patent is extended or adjusted under 35 U.S.C. 154(b) by 397 days.

(21) Appl. No.: 11/015,033

(22) Filed: Dec. 20, 2004

Related U.S. Application Data (63) Continuation-in-part of application No. 10/884,962, filed on Jul. 7, 2004, now abandoned.

(60) Provisional application No. 60/484,640, filed on Jul. 7, 2003.

(51) Int. Cl.
*A61B 5/00* (2006.01)
(52) U.S. Cl. .................. 600/490; 600/500; 600/494
(58) Field of Classification Search .............. 600/300, 600/301, 481, 485, 490, 500, 504
See application file for complete search history.

(56) References Cited

U.S. PATENT DOCUMENTS

| | | | | |
|---|---|---|---|---|
| 4,592,365 | A * | 6/1986 | Georgi | 600/493 |
| 4,718,428 | A * | 1/1988 | Russell | 600/492 |
| 4,870,973 | A * | 10/1989 | Ueno | 600/493 |
| 5,165,416 | A | 11/1992 | Shinoda et al. | |
| 5,533,511 | A * | 7/1996 | Kaspari et al. | 600/485 |
| 5,776,071 | A * | 7/1998 | Inukai et al. | 600/493 |
| 6,190,325 | B1 * | 2/2001 | Narimatsu | 600/490 |
| 6,196,974 | B1 | 3/2001 | Miwa | |
| 6,577,892 | B2 * | 6/2003 | Schomburg | 600/509 |
| 6,599,251 | B2 | 7/2003 | Chen et al. | |
| 2002/0095090 | A1 * | 7/2002 | Caro et al. | 600/485 |
| 2003/0135124 | A1 * | 7/2003 | Russell | 600/500 |

FOREIGN PATENT DOCUMENTS

WO    WO 96/11625    4/1996

* cited by examiner

*Primary Examiner*—Robert L Nasser
(74) *Attorney, Agent, or Firm*—Oyen Wiggs Green & Mutala LLP

(57) ABSTRACT

A blood pressure measurement system is configured to perform a calibration automatically when a calibration condition is satisfied. The calibration condition is based upon one or more parameters of pulse waves of a subject. The parameters may include pulse wave area; a time difference between systolic peak and reflected wave peak or dichrotic notch in the pulse wave and a shape of at least a portion of the pulse wave.

52 Claims, 3 Drawing Sheets

CONTINUOUS NON-INVASIVE BLOOD PRESSURE MEASUREMENT APPARATUS AND METHODS PROVIDING AUTOMATIC RECALIBRATION

CROSS REFERENCE TO RELATED APPLICATION

This application claims the benefit of the filing date of U.S. application No. 60/484,640 filed on Jul. 7, 2003 and entitled CONTINUOUS NON-INVASIVE BLOOD PRESSURE MEASUREMENT APPARATUS AND METHODS PROVIDING AUTOMATIC RECALIBRATION and is a continuation-in-part of U.S. application Ser. No. 10/884,962.

FIELD OF THE INVENTION

This invention relates to apparatus for continuous non-invasive blood pressure (CNIBP) measurement.

BACKGROUND

There are various devices for measuring the blood pressure of subjects in a continuous and non-invasive manner. Some such devices exploit the fact that the pulse transit time (or speed of propagation of heart pulse waves, or pulse wave velocity) varies with blood pressure (and a number of other factors). If all other factors are equal then one can track changes in blood pressure by monitoring the pulse transit time or the speed at which pressure pulses propagate. One device which exploits this principle is described in U.S. Pat. No. 6,599,251 entitled CONTINUOUS NON-INVASIVE BLOOD PRESSURE MONITORING METHOD AND APPARATUS, which is hereby incorporated herein by reference. This device determines blood pressure based on a differential pulse transit time (DPTT) which is measured between two pulse waveforms obtained from two pulse signal detectors, for example optical pulse oximetry sensors, at two peripheral sites on a subject. DPTT is inversely proportional to the pulse propagation speed or pulse wave velocity. An increasing DPTT reflects a decreasing pulse propagation speed and an increasing blood pressure, and vice versa.

One issue with such CNIBP devices is that there are a large number of interacting factors which can effect the pulse propagation speed (or pulse wave velocity) or DPTT. These factors include:
- the effects of vasoactive drug administration which alters the compliance of the arteries,
- changes in the subject's physical position,
- changes of sensor locations,
- changes in the subject's blood density, and so on.

Because the condition of a subject can vary over time the relationship between blood pressure and pulse propagation speed (or pulse wave velocity) or DPTT can also vary over time. It is therefore necessary to recalibrate blood pressure measurement systems which rely on pulse propagation speed (or pulse wave velocity) or DPTT measurements. Recalibration involves taking one or more reference blood pressure measurements. Reference blood pressure measurements may be obtained by way of any suitable alternative blood pressure measurement system such as a cuff-based system, an oscillometric blood pressure measurement mechanism, or the like. The reference blood pressure measurements can be used to redetermine coefficients in a CNIBP calculation formula which, for example, relates DPTT to blood pressure.

It is difficult to predict when the cumulative effect of factors which can affect the calculation that relates blood pressure to DPTT or pulse wave velocity of a CNIBP system is sufficient to require that the system be recalibrated. This is especially true in the environments in which such systems are often used. There is no simple rule for when to manually recalibrate a CNIBP system which takes into account all the effects that may lead to changes to the relationship between blood pressure and the pulse propagation speed (or pulse wave velocity) or DPTT. There is, therefore, a need for systems capable of reliably triggering recalibration when necessary.

SUMMARY OF THE INVENTION

This invention provides CNIBP methods and apparatus which automatically determine when it is necessary to perform a recalibration. The methods and apparatus monitor features of pulse waves in a subject and initiate recalibration when the monitored features differ from corresponding reference features in a stored template.

A first aspect of the invention provides a method for maintaining calibration of a continuous non-invasive blood pressure (CNIBP) measurement system. The method comprises performing a calibration by: obtaining for a subject a reference blood pressure value, reference CNIBP data (e.g. DPTT or pulse wave velocity) at the point reference blood pressure is taken and reference pulse wave data; calculating and storing coefficients of a CNIBP calculation formula based on the reference blood pressure value and the reference CNIBP data; and, storing a template comprising information characterizing one or more characteristics of the reference pulse wave data. The reference pulse wave data corresponds to one or more reference pulse waves and is used for determining when recalibration should be triggered. Subsequently, the method obtains subsequent pulse wave data characterizing one or more subsequent pulse waves of the subject and evaluates a recalibration condition comparing the subsequent pulse wave data to the template. If the subsequent pulse wave data and template satisfy the recalibration condition, the method repeats performing the calibration of the CNIBP measurement system.

Another aspect of the invention provides apparatus for continuous non-invasive blood pressure (CNIBP) measurement. The apparatus comprises: a reference blood pressure measurement mechanism; at least one CNIBP sensor having an output signal which varies with a blood pressure of a subject; and a CNIBP controller. The CNIBP controller is configured to compute a blood pressure of the subject from the output signal according to a CNIBP calculation formula comprising at least one coefficient. The CNIBP controller is configured to trigger the reference blood pressure measurement mechanism to obtain a reference blood pressure and to use the reference blood pressure to determine a new value for the at least one coefficient by: monitoring a pulse wave signal representing pulse waves of the subject; valuating a recalibration condition comparing pulse waves in the pulse wave signal to a stored template; and, determining whether the pulse waves and template satisfy the recalibration condition.

Further aspects of the invention and features of various embodiments of the invention are set out below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
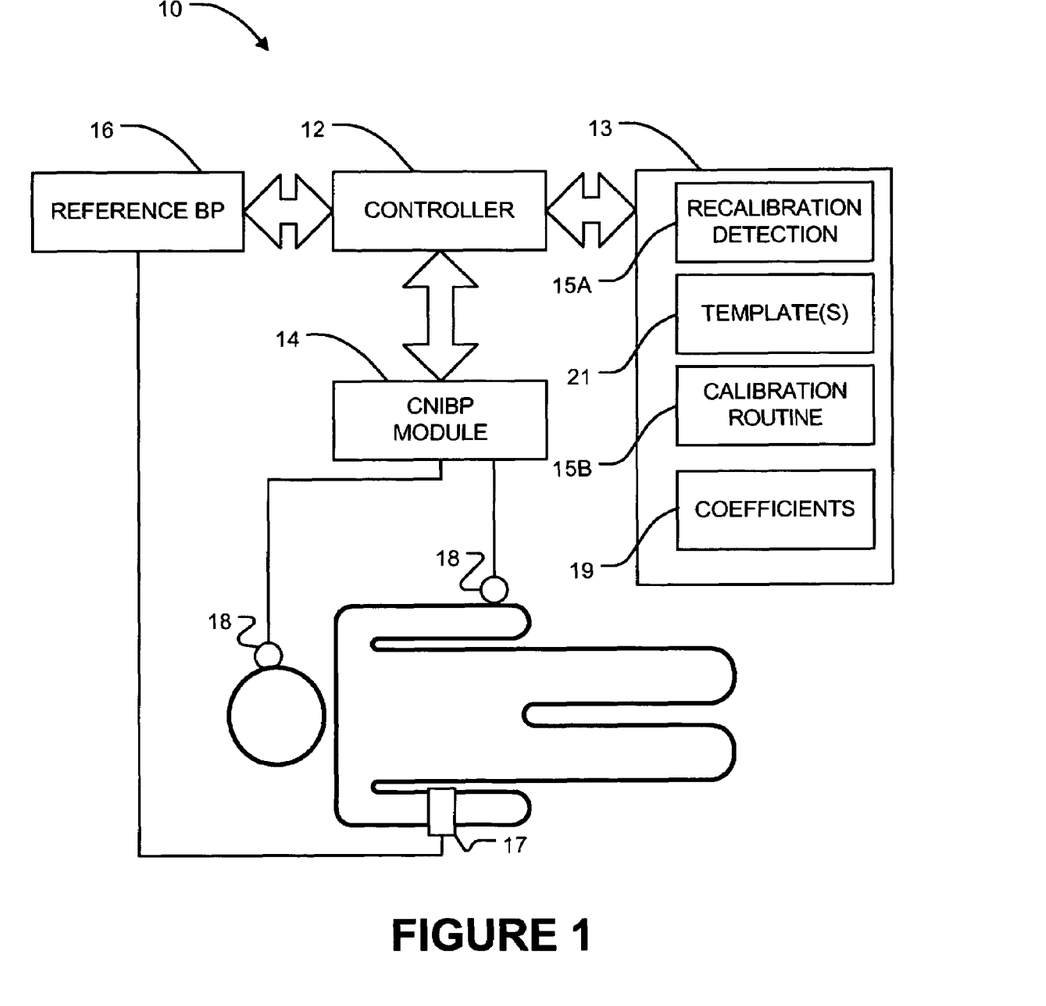
FIG. 1 is a block diagram of a CNIBP measurement system.

FIG. 1 shows a CNIBP measurement system 10 according to the invention. System 10 includes a CNIBP controller 12 which controls the operation of CNIBP measurement system 10. CNIBP controller 12 also controls the operation of a reference blood pressure measurement module 16. CNIBP controller 12 has access to a data store 13. Data store 13 may comprise a combination of storage devices accessible to CNIBP controller 12 and may include registers and other embedded memory in a processor or other devices within CNIBP controller 12. CNIBP controller 12 executes computer software instructions of recalibration detection software 15A. Under the control of software 15A, CNIBP controller 12 monitors a number of parameters and determines from the monitored parameters whether it is appropriate to trigger a recalibration of system 10.

If CNIBP controller 12 determines that it is appropriate to recalibrate system 10 then CNIBP controller 12 triggers the operation of a calibration routine 15B. Under the control of calibration routine 15B, CNIBP controller 12 causes reference blood pressure measurement module 16 to obtain a reference measurement of the subject's blood pressure. Based upon the reference measurement, CNIBP controller 12 determines new coefficients 19 for a blood pressure calculation formula. CNIBP controller 12 stores the new coefficients in data store 13.

In the illustrated embodiment, reference blood pressure measurement module 16 includes a blood pressure detecting means 17 which may include one or more sensors. Blood pressure detecting means 17 comprises any suitable detector for obtaining a reliable measurement of blood pressure. For example, blood pressure detecting means 17 may comprise: a cuff-based system, an oscillometric blood pressure measurement mechanism, or the like. Various blood pressure measurement systems suitable for use as blood pressure detecting means 17 are known.

Under control of calibration routine 15B, CNIBP controller 12 uses a reference blood pressure based upon a signal from blood pressure detecting means 17 to calibrate CNIBP measurement system 10. Calibration involves determining new coefficients for a CNIBP calculation formula that presents the relationship between blood pressure and pulse propagation speed (or pulse wave velocity) or DPTT. Subsequently, CNIBP measurement system 10 operates using the new coefficients to provide measurements of the subject's blood pressure until the next time recalibration detection software 15A determines that it is necessary to recalibrate system 10.

In an example embodiment of the invention, system 10 receives a signal from a sensor which detects pulse waves in a subject. In the illustrated embodiment of the invention, system 10 includes at least two sensors 18 which detect pulse waves on the subject. In the illustrated embodiment, pulse waves are detected by the same sensors 18 which also provide inputs for CNIBP measurement system 10. The illustrated system 10 detects a pulse wave at each of sensors 18 and determines blood pressure, at least in part, from a difference in the times at which the pulse wave arrives at sensors 18.

Figure 2:
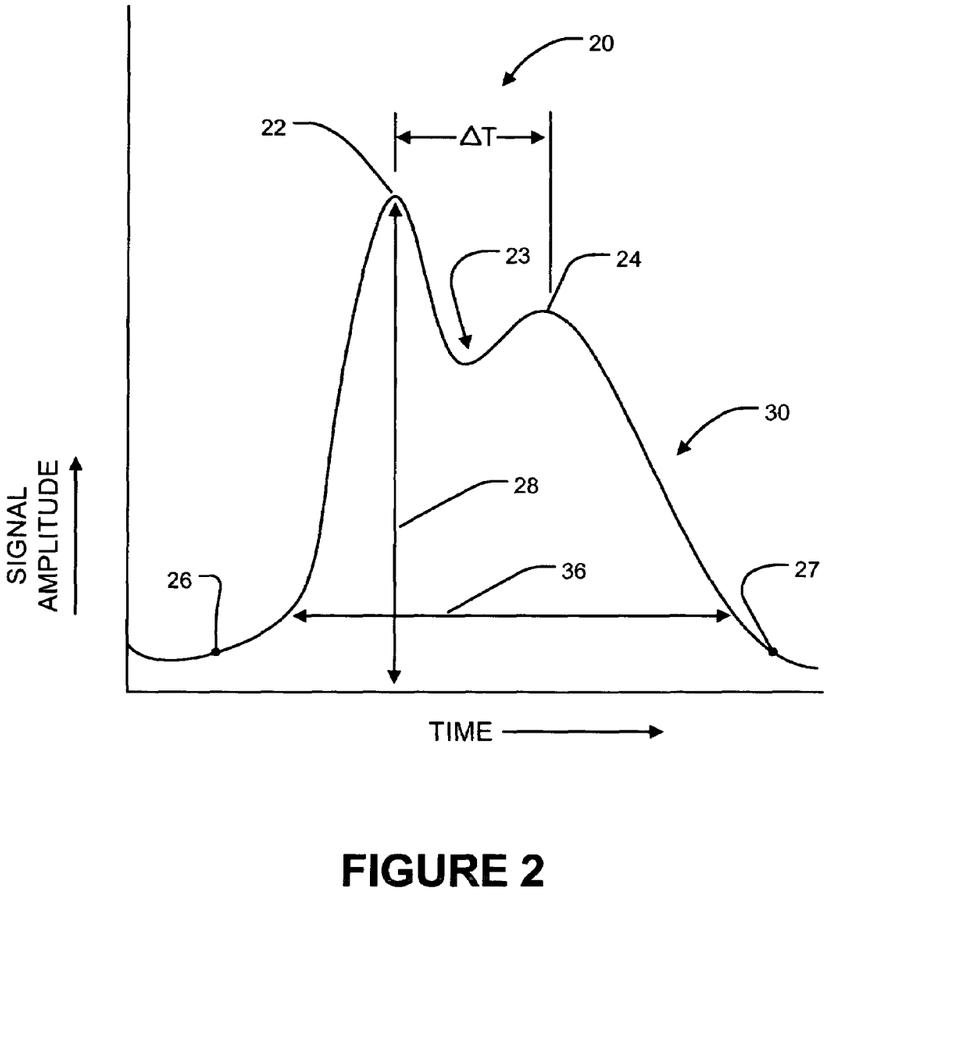
FIG. 2 is a plot of a pulse signal.

CNIBP controller 12 monitors a number of features of the pulse waves. FIG. 2 is an example of a pulse wave signal 20 as might be detected by a pulse-oximetry-type sensor associated with CNIBP measurement system 10. Pulse wave 20 has a systolic peak 22, a dichrotic notch 23 and a reflected wave peak 24. Pulse wave signal 20 may be digitized. In the illustrated embodiment, a CNIBP module 14 includes appropriate signal processing electronics and analog to digital converter(s) (not shown) to acquire and digitize signals from sensors 18 and to make the digitized signals available to CNIBP controller 12. Those skilled in the art are familiar with the design and construction of circuits for the acquisition and digitization of signals from sensors such as pulse-oximetry-type sensors.

Figure 3:
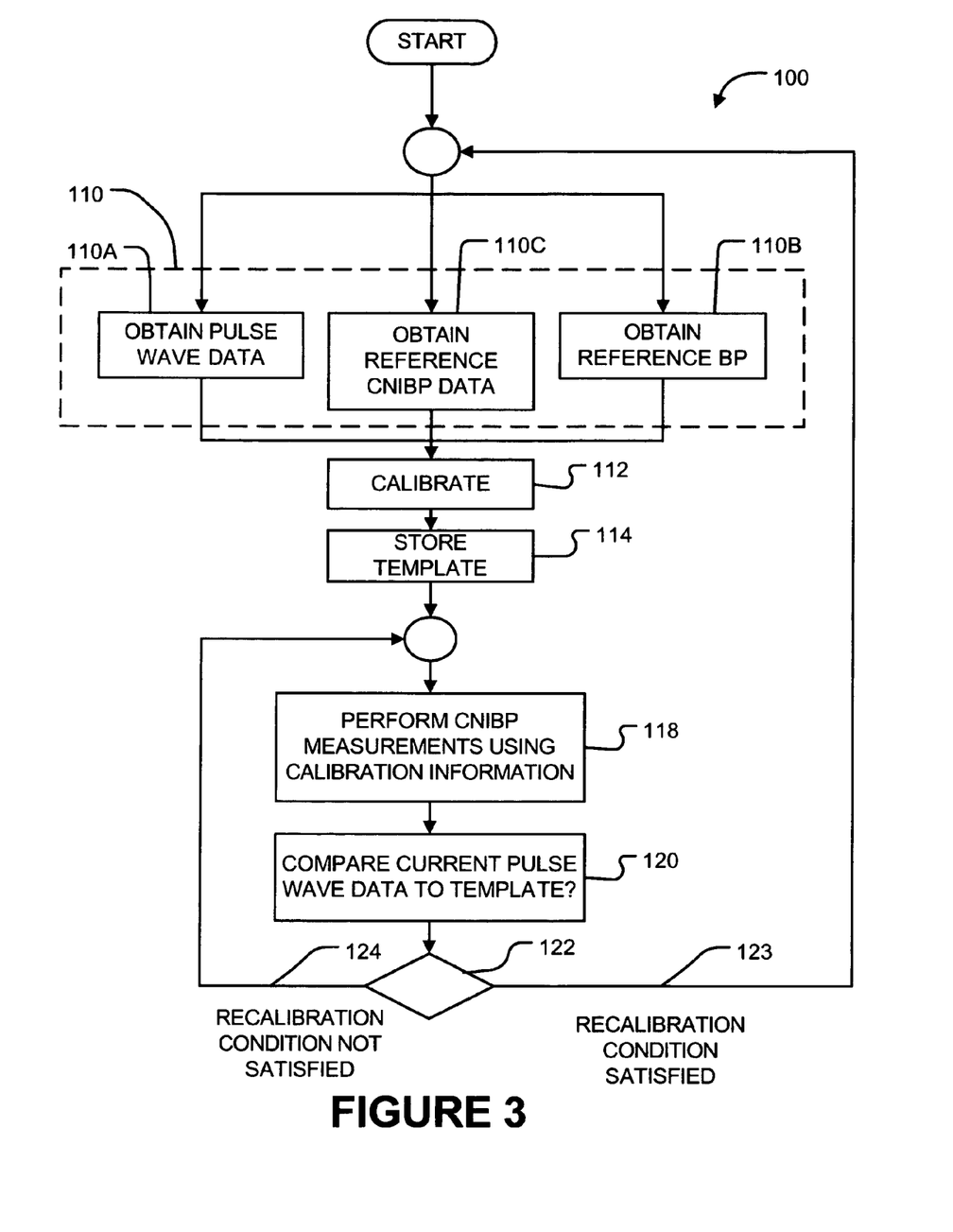
FIG. 3 is a flow chart illustrating a method according to the invention.

Pulse wave 20 has a number of features. These features are illustrated in FIG. 3. One feature of pulse wave 20 is its area.

A second feature of pulse wave 20 is the height of systolic peak, or "pulse amplitude", 22. In FIG. 2 the pulse amplitude is indicated by arrow 28.

A third feature of pulse wave 20 is the shape of pulse wave 20. The shape of the portion 30 of pulse wave 20 is believed to be especially sensitive to at least some factors that can make recalibration necessary in its portion 30 between systolic peak 22 and end point 27.

A fourth feature is the time differences, $\Delta T$, between systolic peak 22 and reflected wave peak 24 and/or between systolic peak 22 and dichrotic notch 23.

In one embodiment of the invention CNBIP measurement system 10 is calibrated in an initial calibration. During the initial calibration, each of the above features, the pulse wave area, the pulse height, the time, $\Delta T$ between the systolic peak 22 and reflected wave peak 24 or dichrotic notch 23, and the shape of portion 30 of pulse wave 20 are each characterized. Information characterizing these features is stored as a collection of parameters in data store 13. The stored collection of these parameters may be called a template 21 (see FIG. 1).

Periodically, for example on each heartbeat, or after each group of several heartbeats, or at spaced apart times, each of the parameters is determined for a current pulse wave, or a current group of pulse waves, and the result is compared to a stored template 21. Typically stored template 21 is a template stored at a time of the most recent calibration. If the difference between the measured parameters and the parameters of the stored template 21 exceeds a threshold according to a suitable metric then a recalibration is triggered.

Various metrics may be used to quantify the difference between a set of parameters measured at a particular time and the corresponding parameters of a stored template 21. In simple cases, each of the parameters is compared to its counterpart in the stored template 21. In the alternative, particular combinations of the parameters, or information derived from the parameters, may be compared to one another.

The stored template 21 may constitute raw stored measured parameter values, stored pulse wave data from which those parameter values can be determined, or the result of one or more calculations based upon the measured parameter values.

The shape of part 30 of waveform 20 may be recorded, for example, by storing a number of points from portion 30 of the waveform in a data store. When a subsequent measurement is made of the shape of portion 30 of a subsequent pulse wave, the difference can be computed, for example, as:

an average of the absolute values of differences between corresponding ones of the points on the two pulse waves;

an average of the sum of squares of differences between corresponding ones of the points of the two pulse waves;

the result of another correlation calculation between a subsequent measurement and the stored template 21;

fitting a fitting function to each of the two pulse waves and comparing coefficients of the fitted fitting function;

some combination of these; or the like.

The area of pulse wave 20 may be determined by integrating pulse wave 20 between a chosen start point 26, and a suitably chosen end point 27. The end point may, for example, be at the consequent diastolic valley. The start point may, for example, be at the foot of the pulse wave or the diastolic valley.

Instead of integrating the area of a pulse wave 20, CNIBP controller 12 could measure the height and width of a pulse wave 20 as indicated by arrows 28 and 36 in FIG. 2. The product of height and width measurements could be used in place of the area parameter. If this is done, the measurement indicated by arrow 36 should be taken at a signal amplitude which is smaller than the amplitude of dichrotic notch 23. The amplitude at which width 36 is measured may be a function of the amplitude at one or more points in wave form 20, such as a function of amplitudes at systolic peak 22 and/or reflected wave peak 24. A reference value for pulse wave area may be compared directly to a current value of pulse wave area, for example by subtraction or division.

The time difference ΔT may be determined in any of various suitable ways including:

performing peak detection on raw pulse wave data to identify the systolic peak 22 and reflected wave peak 24 and/or dichrotic notch 23 and to determine how far apart they are in time;

using cross-correlation methods to locate the peaks and/or the notch;

computing a first derivative of pulse wave 20 to find systolic and diastolic peaks 22, 24 and/or either one of the peaks and notch 23;

computing a second derivative of pulse wave 20 to find to find systolic and diastolic peaks 22, 24 and/or either one of the peaks and notch 23;

some combination of these techniques, etc.

A reference value of ΔT may be compared directly to a current value of ΔT, for example by comparing the result of a subtraction or division of the reference and current values of ΔT to a threshold.

If the relationship between the reference parameters of the template and the current parameters satisfies a recalibration condition then CNIBP controller 12 initiates a recalibration routine. The recalibration condition may include comparing a current value of one or more of the above parameters to a corresponding value from a stored template. The condition may be the logical "OR" of two or more sub-conditions. The sub-conditions may include, for example, two or more of:

the difference in the area parameter exceeds a first threshold;

the difference in the ΔT parameter exceeds a second threshold;

the difference in the shape parameter exceeds a third threshold;

an average or weighted average of differences in two or more of the area, ΔT and shape parameters exceeds a fourth threshold;

and so on.

The sub-conditions could also include one or more additional sub-conditions such as:

more than a specified time has passed since the most recent recalibration;

the calculated value for the subject's blood pressure differs from the most-recently-obtained reference blood pressure by more than a threshold amount (for example ±30%);

an average rate of change of the subject's calculated blood pressure has exceeded a threshold amount over a predetermined period;

some combination of these sub-conditions etc.

Optionally system 10 includes a first mechanism for triggering recalibration based upon features of pulse wave 20 and a second mechanism for triggering recalibration on the basis of time since the last recalibration.

FIG. 3 illustrates a method 100 according to the invention. In block 110, method 100 acquires pulse wave data (block 110A) for later use in determining whether recalibration is necessary, a reference blood pressure value (block 110B) and reference CNIBP data (block 110C) for determining CNIBP calculation coefficients in calibration. In block 112, the reference blood pressure and the pulse wave or DPTT data are used to derive calibration information for CNIBP measurement system 10. The calibration information may comprise, for example, one or more parameters which affect the CNIBP calculation of the subject's blood pressure.

In block 114 a template 21 is stored. The template is based upon the pulse wave information obtained in block 110A. Block 114 may be performed at any time after the pulse wave information has been obtained. Block 114 may be performed prior to, after or simultaneously with the calibration performed in block 112. The data stored in block 114 may be combined values (e.g. combined by averaging) describing characteristics of one or more pulse waves taken during the calibration process.

In block 118 CNIBP measurements are performed using the calibration information determined in block 112. The CNIBP measurements are periodically updated. The CNIBP data may be obtained, for example, each time a single or multiple heartbeats are detected at sensors 18 (see FIG. 1).

In block 120, current pulse wave data is obtained, processed if necessary, and compared to the template which was stored in block 114. Block 122 determines whether or not a recalibration condition, which is based upon the pulse wave data and the stored template 21, is satisfied. If block 122 determines that the recalibration condition is satisfied then method 100 loops back to perform another calibration on path 123. If block 122 discovers that the recalibration condition is not satisfied then method 100 loops back to continue performing CNIBP measurements on path 124.

In some embodiments of the invention, the recalibration condition and/or one or more sub-conditions of the recalibration condition include a parameter that affects the sensitivity of the condition or sub-condition. Whether or not the condition or sub-condition is satisfied depends upon the current value of the sensitivity parameter, the value(s) used as inputs for the condition or sub-condition and any threshold(s) used in evaluating the condition or sub-condition. For example, where a sub-condition compares a number derived from a feature of a waveform to a threshold, the sensitivity parameter may comprise a factor that adds to, subtracts from, multiplies or divides the threshold and/or the derived number being compared to the threshold. The value of the sensitivity factor affects what values for the derived number will cause the condition or sub-condition to be satisfied.

Separate sensitivity parameters may be provided for each of a plurality of sub-conditions. Apparatus according to the invention may provide an interface which permits a user to vary one or more sensitivity parameters. A single user input may simultaneously control values of multiple sensitivity parameters.

In some cases, motion artifacts could cause system 10 to measure values that result in a recalibration condition to being satisfied in a case where the condition would not be satisfied in the absence of the motion artifact.

System 10 may comprise an artifact detecting mechanism, that monitors the signals received from sensors 18 for characteristics which tend to indicate the presence of motion artifacts. For example some motion artifacts include components much higher and/or much lower frequencies than heartbeat frequencies. Some motion artifacts have characteristic waveforms. Motion artifacts can result in rapid fluctuations in DPTT. The artifact detecting mechanism could include one or more of:

A mechanism that detects high and/or low frequency components in the pulse wave signal(s). For example, software or hardware that performs a time-to-frequency domain transformation such as a fast Fourier transform on one or more of the signals being monitored;

A mechanism that attempts to match a waveform of one or more of the signals being monitored to patterns characteristic of motion artifacts. For example, software or hardware that performs pattern matching; and, A mechanism that detects rapid variations in measured DPTT. For example, the mechanism may detect whether DPTT varies by more than a threshold amount, for example ±20%, between adjacent pulses.

The artifact detecting mechanism may comprise a software routine and/or suitable hardware. The artifact detecting mechanism may trigger a timer upon an artifact being detected.

In some embodiments of the invention the artifact detection mechanism suppresses recalibration being triggered or, in the alternative suppresses recalibration being triggered by one or more selected sub-conditions, for a predetermined time after an artifact is detected. In some embodiments system 10 is configured to trigger recalibration, even if recalibration would not otherwise be triggered, in cases where artifacts are detected over a significant period. For example, upon detection of a motion artifact, system 10 may suppress recalibration for a first time period, for example a period in the range of 5-45 seconds, typically about 30 seconds. If artifacts continue to be detected so that recalibration is still being suppressed at the end of a second, longer, time period, for example a time period in the range of 45 seconds to 1 or 2 minutes, then system 10 may trigger a recalibration.

In some instances the artifact detection mechanism may detect a motion artifact while a calibration is being performed. Systems according to some embodiments of the invention are configured to ignore results of the calibration being performed in response to the detection of a motion artifact. Such systems may terminate the acquisition of a blood pressure by reference blood pressure measurement module 16 in response to the detection of a motion artifact. In response to detection of the motion artifact, the system may suppress recalibration for a short period, as described above, and/or schedule the interrupted calibration to be performed after a suitable interval which is long enough for effects of the motion artifact to have subsided and is also long enough to permit blood pressure measurement module 16 to be reset, if necessary.

Certain implementations of the invention comprise computer processors which execute software instructions which cause the processors to perform a method of the invention. For example, one or more processors in a CNIBP controller may implement the methods of FIG. 3 by executing software instructions in a program memory accessible to the processors. The invention may also be provided in the form of a program product. The program product may comprise any medium which carries a set of computer-readable signals comprising instructions which, when executed by a computer processor, cause the processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, RAM, flash RAM, or the like. The instructions may optionally be stored on the medium in a compressed and/or encrypted format.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

in some embodiments of the invention, a template may be stored for each of a number of different prior calibration events. Measured parameters may be compared to each of the stored templates to find a stored template which is closest to the measured parameters. A calibration associated with that closest template may be used. In such embodiments of the invention recalibration may be triggered only if the measured parameters are sufficiently different from all of the stored templates. The stored templates may each expire and be deleted after a given time.

The templates are not necessarily based upon data for a single pulse wave. Templates may be constructed from data from several pulse waves which may be combined by averaging or the like.

The recalibration condition need not be based on data from a single pulse wave but may involve comparing data derived from two or more pulse waves to a template.

In some embodiments of the invention a recalibration system generates a signal which indicates that recalibration should be initiated manually rather than automatically performing the recalibration.

The invention may be embodied in a module which generates a signal which may be used to trigger recalibration of a separate CNIBP system.

Accordingly, the scope of the invention is to be construed in accordance with the substance defined by the following claims.

What is claimed is:

1. A method for maintaining calibration of a continuous non-invasive blood pressure (CNIBP) measurement system, the method comprising:

performing a calibration by:

obtaining for a subject a reference blood pressure value, reference CNIBP data and reference pulse wave data, the reference pulse wave data corresponding to one or more reference pulse waves of the subject and having a waveform;

calculating and storing coefficients of a CNIBP calculation formula based on the reference blood pressure value and the reference CNIBP data; and, storing a template comprising information characterizing a plurality of characteristics of the waveform of the reference pulse wave data;

subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system, wherein the recalibration condition comprises a sensitivity parameter and the sensitivity parameter affects whether or not the subsequent pulse wave data and template satisfy the recalibration condition.

2. A method according to claim 1 wherein the reference CNIBP data comprises differential pulse transit time data or pulse wave velocity data.

3. A method according to claim 2 wherein the differential pulse transit time data comprises first and second signals from first and second sensors, and the reference pulse wave data and subsequent pulse wave data are derived at least in part from one of the first and second signals.

4. A method according to claim 3 wherein the first and second sensors are pulse-oximetry-type sensors.

5. A method according to claim 1 wherein the pulse wave recalibration condition is based, at least in part, on at least one of a first feature, a second feature and a third feature of the reference and subsequent pulse waves:

the first feature comprising a pulse wave area of the reference and subsequent pulse waves;

the second feature comprising a time difference, $\Delta T$, between two internal features within the reference and subsequent pulse waves; and, the third feature comprising a pulse wave shape of the reference and subsequent pulse waves.

6. A method according to claim 5 wherein the recalibration condition is based on a plurality of the first, second and third features.

7. A method according to claim 5 wherein the recalibration condition is based in part on a pulse amplitude of one or more of the reference pulse waves.

8. A method according to claim 5 wherein the recalibration condition is based in part on a pulse width of one or more of the reference pulse waves.

9. A method according to claim 1 wherein the pulse wave recalibration condition is based, at least in part, on a comparison of a pulse wave area of one or more of the one or more reference pulse waves to a pulse wave area of one or more of the subsequent pulse waves.

10. A method according to claim 9 wherein the pulse wave recalibration condition comprises comparing a difference between the pulse wave area of the one or more of the one or more reference pulse waves and a pulse wave area of one or more of the subsequent pulse waves to a first threshold.

11. A method according to claim 9 wherein the pulse wave recalibration condition comprises comparing a ratio of the pulse wave area of the one or more of the one or more reference pulse waves and a pulse wave area of one or more of the subsequent pulse waves to a first threshold.

12. A method according to claim 9 wherein the reference CNIBP data comprises differential pulse transit time data or pulse wave velocity data.

13. A method according to claim 12 wherein the differential pulse transit time data comprises first and second signals from first and second sensors, and the reference pulse wave data and subsequent pulse wave data are derived at least in part from one of the first and second signals.

14. A method according to claim 9 comprising determining the pulse wave areas of the reference and subsequent pulse waves by integration.

15. A method according to claim 9 comprising determining the pulse wave areas of each of the reference and subsequent pulse waves by multiplying a pulse height by a pulse width, the pulse width measured at an amplitude lower than dichrotic notches of the reference and subsequent pulse waves.

16. A method according to claim 1 wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves.

17. A method according to claim 1 wherein the pulse wave recalibration condition is based, at least in part, on a comparison of a shape of one or more of the reference pulse waves to a shape of one or more of the subsequent pulse waves.

18. A method according to claim 17 comprising comparing the shape of the reference pulse waves to a shape of the subsequent pulse waves by a method comprising computing an average of the absolute values of differences between corresponding ones of the points on the reference and subsequent pulse waves.

19. A method according to claim 17 comprising comparing the shape of the reference pulse waves to a shape of the subsequent pulse waves by a method comprising computing an average of the sum of squares of differences between corresponding ones of the points of the reference and subsequent pulse waves.

20. A method according to claim 17 comprising comparing the shape of the reference pulse waves to a shape of the subsequent pulse waves by a method comprising computing the result of a correlation calculation between corresponding ones of the points of the reference and subsequent pulse waves.

21. A method according to claim 1 wherein the pulse wave recalibration condition is based, at least in part, on a comparison of a pulse wave amplitude of one or more of the one or more reference pulse waves to a pulse wave amplitude of one or more of the subsequent pulse waves.

22. A method according to claim 1 wherein the pulse wave recalibration condition is based, at least in part, on a comparison of a pulse width of one or more of the one or more reference pulse waves to a pulse width of one or more of the subsequent pulse waves.

23. A method according to claim 1 comprising automatically repeating performing the calibration of the CNIBP measurement system whenever more than a specified time has passed since the most recent recalibration.

24. A method according to claim 1 comprising automatically repeating performing the calibration of the CNIBP measurement system when a value for the subject's blood pressure determined by the CNIBP calculation formula differs from the most-recently-obtained reference blood pressure by more than a threshold amount.

25. A method according to claim 1 comprising automatically repeating performing the calibration of the CNIBP measurement system when an average rate of change of the subject's blood pressure determined by the CNIBP calculation formula exceeds a threshold amount over a predetermined period.

26. A method according to claim 1 wherein the recalibration condition comprises a plurality of sub-conditions and the value of the sensitivity parameter affects whether or not the subsequent pulse wave data and template satisfy each of a plurality of the plurality of sub-conditions.

27. A method according to claim 1 comprising detecting the presence of a motion artifact in the subsequent pulse wave data and, in response to the detection of the motion artifact, suppressing repeating performing the calibration of the CNIBP measurement system for a time period.

28. A method according to claim 1 comprising detecting a motion artifact while repeating performing the calibration of the CNIBP measurement system and, in response thereto, ignoring any result of repeating performing the calibration of the CNIBP measurement system and automatically repeating performing the calibration of the CNIBP measurement system after a time period.

29. A method for maintaining calibration of a continuous non-invasive blood pressure (CNIBP) measurement system, the method comprising:
performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;
subsequently, obtaining subsequent pulse wave data characterizing one or more subsequent pulse waves of the subject and evaluating a recalibration condition comparing characteristics of a waveform of the subsequent pulse waves to the template; and,
if the subsequent pulse wave data and template satisfy the recalibration condition, repeating performing the calibration of the CNIBP measurement system;
wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and wherein the two internal features are systolic and reflected wave peaks of the reference and subsequent pulse waves.

30. A method according to claim 29 comprising comparing a difference between or a ratio of $\Delta T$ for the reference and subsequent pulse waves to a second threshold.

31. A method for maintaining calibration of a continuous non-invasive blood pressure (CNIBP) measurement system, the method comprising:
performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;
subsequently, obtaining subsequent pulse wave data characterizing one or more subsequent pulse waves of the subject and evaluating a recalibration condition comparing characteristics of a waveform of the subsequent pulse waves to the template; and,
if the subsequent pulse wave data and template satisfy the recalibration condition, repeating performing the calibration of the CNIBP measurement system;
wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and wherein the two internal features are a systolic peak and a dichrotic notch of the reference and subsequent pulse waves.

32. A method for maintaining calibration of a continuous non-invasive blood pressure (CNIBP) measurement system, the method comprising:
performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;
subsequently, obtaining subsequent pulse wave data characterizing one or more subsequent pulse waves of the subject and evaluating a recalibration condition comparing characteristics of a waveform of the subsequent pulse waves to the template; and,
if the subsequent pulse wave data and template satisfy the recalibration condition, repeating performing the calibration of the CNIBP measurement system;
wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and wherein the two internal features are a reflected wave peak and a dichrotic notch of the reference and subsequent pulse waves.

33. A method for maintaining calibration of a continuous non-invasive blood pressure (CNIBP) measurement system, the method comprising:
performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;
subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system;

wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and the method comprises, for each of the reference and subsequent pulse waves, performing peak detection to locate at least two of a systolic peak, a reflected wave peak and a dichrotic notch.

34. A method for maintaining calibration of a continuous non-invasive blood pressure (CNIBP) measurement system, the method comprising:

performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;

subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system;

wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and the method comprises, for each of the reference and subsequent pulse waves, locating at least two of a systolic peak, a reflected wave peak and a dichrotic notch by way of a cross-correlation method.

35. A method for maintaining calibration of a continuous non-invasive blood pressure (CNIBP) measurement system, the method comprising:

performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;

subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system;

wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and the method comprises, for each of the reference and subsequent pulse waves, computing a first derivative of the pulse wave and, based at least in part on the first derivative, locating at least two of a systolic peak, a reflected wave peak and a dichrotic notch.

36. A method for maintaining calibration of a continuous non-invasive blood pressure (CNIBP) measurement system, the method comprising:

performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;

subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system;

wherein the pulse wave recalibration condition is based, at least in part, on a comparison of a time difference, $\Delta T$, between two internal features within one of the reference pulse waves and a time difference, $\Delta T$, between two corresponding internal features within one of the subsequent pulse waves, and the method comprises, for each of the reference and subsequent pulse waves, computing a second derivative of the pulse wave and, based at least in part on the second derivative, locating at least two of a systolic peak, a reflected wave peak and a dichrotic notch.

37. A method for maintaining calibration of a continuous non-invasive blood pressure (CNIBP) measurement system, the method comprising:

performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave data;

subsequently, obtaining subsequent pulse wave data characterizing one or more subsequent pulse waves of the subject and evaluating a recalibration condition comparing characteristics of a waveform of the subsequent pulse waves to the template; and, if the subsequent pulse wave data and template satisfy the recalibration condition, repeating performing the calibration of the CNIBP measurement system, wherein the pulse wave recalibration condition is based, at least in part, on a comparison of a shape of one or more of the reference pulse waves to a shape of one or more of the subsequent pulse waves, and the method comprises, comparing the shape of the reference pulse waves to a shape of the subsequent pulse waves by a method comprising fitting a fitting function to each of the reference and subsequent pulse waves.

38. Apparatus for continuous non-invasive blood pressure (CNIBP) measurement, the apparatus comprising:
a reference blood pressure measurement mechanism;
at least one CNIBP sensor having an output signal which varies with a blood pressure of a subject;
a CNIBP controller configured to compute a blood pressure of the subject from the output signal according to a CNIBP calculation formula comprising at least one coefficient;
wherein the CNIBP controller is configured to trigger the reference blood pressure measurement mechanism to obtain a reference blood pressure and to use the reference blood pressure to determine a new value for the at least one coefficient by:
monitoring a pulse wave signal representing pulse waves of the subject, the pulse waves having waveforms;
evaluating a recalibration condition comparing two or more characteristics of the waveforms of the pulse waves in the pulse wave signal to a stored template; and,
determining whether the pulse waves and template satisfy the recalibration condition,
the apparatus comprising a sensitivity parameter having a value accessible to the controller, the controller configured to evaluate the recalibration condition based in part on the value of the sensitivity parameter.

39. Apparatus according to claim 38 wherein the pulse wave signal is a signal generated by the CNIBP sensor.

40. Apparatus according to claim 38 wherein the CNIBP sensor comprises first and second sensors and the CNIBP formula relates a time interval between a pulse wave being detected at the first and second sensors to the subject's blood pressure.

41. Apparatus according to claim 38 wherein the controller is configured to compute at least two of a first feature, a second feature and a third feature of the reference and subsequent pulse waves:
the first feature comprising a pulse wave area of the pulse waves;
the second feature comprising a time difference, $\Delta T$, between two internal features within the pulse waves; and,
the third feature comprising a pulse wave shape of the pulse waves;
wherein the recalibration is based, at least in part, on the at least two of the first, second and third features.

42. Apparatus according to claim 41 wherein the controller is configured to compute a pulse wave area of the pulse waves and the recalibration condition is satisfied if the pulse wave area differs from a reference pulse wave area in the template by more than a first threshold amount.

43. Apparatus according to claim 41 wherein the controller is configured to compute a time difference, $\Delta T$, between two internal features within the pulse waves and the recalibration condition is satisfied if $\Delta T$ differs from a reference $\Delta T$ in the template by more than a second threshold amount.

44. Apparatus according to claim 41 wherein the controller is configured to compute a value for a comparison function comparing a pulse wave shape of the pulse waves to a reference pulse wave shape in the template and the recalibration condition is satisfied if the comparison function indicates that the pulse wave shape differs from the reference pulse wave shape by more than a third threshold amount.

45. Apparatus according to claim 41 comprising:
means for measuring a pulse wave area of the pulse waves;
means for measuring a time difference, $\Delta T$, between two internal features within the pulse waves; and,
means for measuring a pulse wave shape of the pulse waves.

46. Apparatus according to claim 38 comprising a motion artifact detection mechanism connected to suppress triggering of the reference blood pressure measurement mechanism for a first time period upon detection of a motion artifact in the pulse wave data.

47. Apparatus according to claim 38 wherein the controller is configured to evaluate each of a plurality of sub-conditions of the recalibration condition based in part on the value of the sensitivity parameter.

48. A program product comprising a medium carrying computer-readable instructions which, when executed by a processor, cause the processor to coordinate the performance of a method comprising:
performing a calibration by:
obtaining for a subject a reference blood pressure value, reference CNIBP data and reference pulse wave data, the reference pulse wave data corresponding to one or more reference pulse waves of the subject and having a waveform;
calculating and storing coefficients of a CNIBP calculation formula based on the reference blood pressure value and the reference CNIBP data; and,
storing a template comprising information characterizing a plurality of characteristics of the waveform of the reference pulse wave;
subsequently, obtaining subsequent pulse wave data characterizing one or more subsequent pulse waves of the subject and evaluating a recalibration condition comparing characteristics of a waveform of the subsequent pulse waves to the template; and,
if the subsequent pulse wave data and template satisfy the recalibration condition, repeating performing the calibration of the CNIBP measurement system,
wherein the recalibration condition comprises a sensitivity parameter and the sensitivity parameter affects whether or not the subsequent pulse wave data and template satisfy the recalibration condition.

49. A method for maintaining calibration of a continuous non-invasive blood pressure (CNIBP) measurement system, the method comprising:
performing a calibration by:
obtaining for a subject a reference blood pressure value, reference CNIBP data and reference pulse wave data, the reference pulse wave data corresponding to one or more reference pulse waves;
calculating and storing coefficients of a CNIBP calculation formula based on the reference blood pressure value and the reference CNIBP data; and,
storing a template comprising information characterizing one or more characteristics of the reference pulse wave;

subsequently, obtaining subsequent pulse wave data characterizing one or more subsequent pulse waves of the subject and evaluating a recalibration condition comparing the subsequent pulse wave data to the template; and, if the subsequent pulse wave data and template satisfy the recalibration condition, repeating performing the calibration of the CNIBP measurement system;

wherein the recalibration condition comprises a sensitivity parameter and the sensitivity parameter affects whether or not the subsequent pulse wave data and template satisfy the recalibration condition.

50. A method according to claim 49 wherein the recalibration condition comprises a plurality of sub-conditions and the value of the sensitivity parameter affects whether or not the subsequent pulse wave data and template satisfy each of a plurality of the plurality of sub-conditions.

51. Apparatus for continuous non-invasive blood pressure (CNIBP) measurement, the apparatus comprising:
a reference blood pressure measurement mechanism;
at least one CNIBP sensor having an output signal which varies with a blood pressure of a subject;
a CNIBP controller configured to compute a blood pressure of the subject from the output signal according to a CNIBP calculation formula comprising at least one coefficient;
wherein the CNIBP controller is configured to trigger the reference blood pressure measurement mechanism to obtain a reference blood pressure and to use the reference blood pressure to determine a new value for the at least one coefficient by:
monitoring a pulse wave signal representing pulse waves of the subject;
evaluating a recalibration condition comparing pulse waves in the pulse wave signal to a stored template; and,
determining whether the pulse waves and template satisfy the recalibration condition;
the apparatus comprising a sensitivity parameter having a value accessible to the controller, the controller configured to evaluate the recalibration condition based in part on the value of the sensitivity parameter.

52. Apparatus according to claim 51 wherein the controller is configured to evaluate each of a plurality of sub-conditions of the recalibration condition based in part on the value of the sensitivity parameter.

* * * * *